US00PP07853P

United States Patent [19]

Jessel, Jr.

[11] Patent Number: Plant 7,853

[45] Date of Patent: Apr. 14, 1992

[54] CARNATION PLANT NAMED CFPC HOLIDAY

[75] Inventor: Walter H. Jessel, Jr., Salinas, Calif.

[73] Assignee: California Florida Plant Co., L. P., Salinas, Calif.

[21] Appl. No.: 580,192

[22] Filed: Sep. 10, 1990

[51] Int. Cl.[5] ..... A01H 5/00

[52] U.S. Cl. ..... Plt./70

[58] Field of Search ..... Plt. 70, 73

[56] References Cited

U.S. PATENT DOCUMENTS

| | | | |
|---|---|---|---|
| P.P. 5,410 | 3/1985 | Carrier | Plt. 70 |
| P.P. 5,529 | 8/1985 | Van Andel | Plt. 70 |
| P.P. 6,209 | 6/1988 | Barberet et al. | Plt. 70 |
| P.P. 6,271 | 9/1988 | Barberet et al. | Plt. 70 |

*Primary Examiner*—Howard J. Locker

*Attorney, Agent, or Firm*—Christie, Parker & Hale

[57] ABSTRACT

A new and unusual white carnation with variegated red coloration.

1 Drawing Sheet

BACKGROUND OF THE INVENTION

Carnation varieties producing flowers of many different colors are well known. However, it is desirable to provide a new standard variety of carnation producing flowers having white and red variegated coloration.

The closest variety heretofore known of which I am aware is 'Lonpindi' (U.S. Plant Pat. No. 6,209). The new variety differs from 'Lonpindi' in having a 4 to 5 week earlier flowering response and stronger, less brittle stems. Brittle stems are undesirable because they tend to snap or break when cutting and handling. The flowers of 'CFPC Holiday' are about ¾-inches larger than Lonpindi and flower petal edges of the new variety are deeply serrated in contrast to the comparatively smooth petal edges of Lonpindi flowers. In addition, the new variety has about twenty more flower petals and pinched plants are about 2-inches shorter than Lonpindi.

SUMMARY OF THE INVENTION

The present invention relates to a new and distinct variety of carnation plant which was originated by me in a controlled breeding program by my crossing as seed parent, a numbered but unnamed and unpatented seedling of my creation and as pollen parent, the variety known as 'Carrier's Fiesta' (U.S. Plant Pat. No. 5,410). The varietal denomination of this new carnation is 'CFPC Holiday'.

Among the novel characteristics possessed by the new variety which distinguish it from its parents and all other varieties of which I am aware is the unusual variegated white and red flower coloring and strong stems, in a standard. Flowers of the new variety have early response and excellent vase-life.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety depicted in color as nearly true as it is reasonably possible to make the same in a color illustration of this character.

DESCRIPTION OF THE NEW VARIETY

The new variety, CFPC Holiday, produces flowers which are long lasting after cutting. It has been determined that its vase-life averages 18 to 20-days. The new variety also produces very large standard-type flowers with strong stems on a very vigorous and free-breaking plant. 'CFPC Holiday' also exhibits early flowering response which, together with its attractive variegated coloring and the other characteristics heretofore and hereinafter described, make it especially suitable for commercial cut flower production.

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, and Salinas, Calif. The height of plant and flower and foliage size are established as an average using standard commercial cultural practices.

Name: 'CFPC Holiday'.

Classification:

*Botanical.*—*Dianthus caryophyllus.*

*Commercial.*—Carnation, standard disbud type.

Parentage:

Female parent: Unnamed seedling (No. 0171).

Male parent: 'Carrier's Fiesta'.

PLANT

Height: About 43 to 45 inches.

Growing habit: Herbaceous, semi-upright.

Blooming habit: Terminal as a disbud.

Blooming season: Year round.

Rooting time: 18–20 days.

Breaking action: Excellent.

Mutation prone: No.

Disease resistance: Unknown.
Temperature tolerance: Typical for carnation.

FOLIAGE

Quantity: Numerous.
Shape: Lanceolate.
Texture: Smooth.
Ribs: Central keel.
Arrangement: Bi-lateral along stem
Color:
Upper side.—Near to 189A
*Underside*—Near to 191A
Stem:
*Color.*—Greyed green.

BUD

Shape: Oval.
Color: Near to 191A.
Length: About 1¼ inches.
Diameter: About ⅝ to ¾ inch.

CALYX

Number of lobes (sepals): About 5.
Length: About 1⅓ inches.
Width: About ¾ inch.
Color:
*Outside.*—Near 191A.
*Inside.*—Near 194D.

BLOOM

Shape: Round.
Size:
*Diameter average.*—About 3¾ to 4¾ inches.
Borne: Terminal as disbudded.
Color:
*General tonality.*—White with red variegation.
*Upper side.*—Near to from 155B to whiter than 155D.
*Lower side.*—Same as upper side.
Variegation.—Red variegated markings are from 45D to 45C.
*Outer petals.*—Whiter than 155D.
Permanence: Yes.
Keeping Habit: Excellent.

Fragrance: None.

PETALS

Number: About 72 as compared to about 52 in Lonpindi'
Outer petals:
*Length.*—About 2¼ inches.
*Width.*—About 1½ inches.
Central petals:
*Length.*—About 1½ inches.
*Width.*—About ¾ inches.
Texture: Smooth.
Form: Fan shaped.

REPRODUCTIVE ORGANS

Stamen:
*Number.*—About 12-14.
Arrangement.—Around the ovary.
Anthers:
*Number.*—About 12-14.
*Length.*—About ⅛ inch.
*Color.*—Near to 160D.
Filaments:
*Length.*—About 1 inch.
*Color.*—Near to 158D.
Pistil:
*Number.*—About 3.
*Length.*—About 1½inches.
*Color.*—Style — near to 158D.
Stigma:
*Number.*—About 3.
*Color.*—White.
Fertility:
*Male.*—Sterile.
*Female.*—Poor — fair.
Ovary:
*Shape.*—Concial, ribbed.
*Color.*—Base — greenish white. Body — greenish yellow. Apex — tan.

I claim:

1. A new and distinct variety of carnation plant, substantially as shown and described, characterized particularly by flowers of attractive white and red variegated coloration and strong stems.

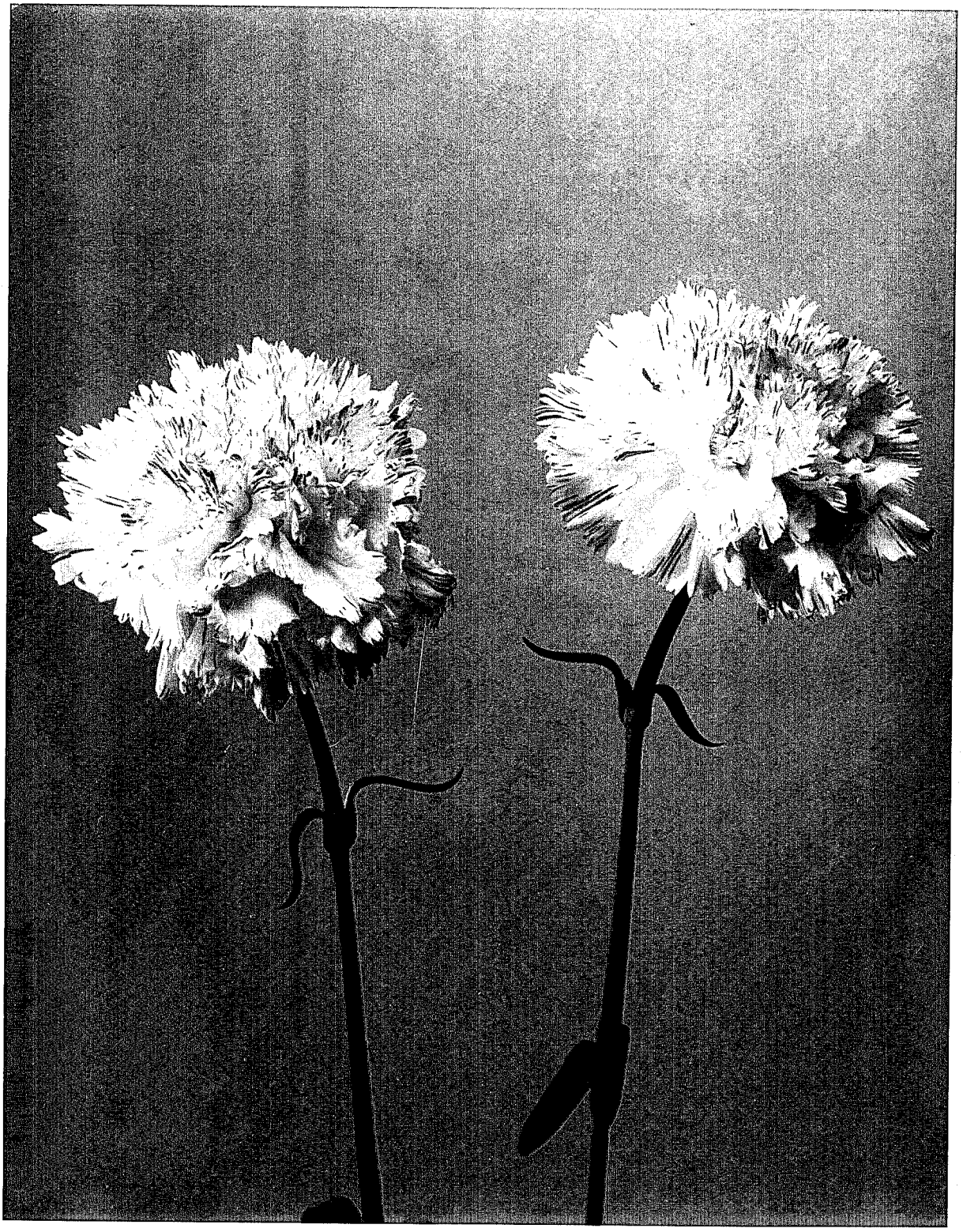

* * * * *